United States Patent

Koster et al.

[11] 3,985,746
[45] Oct. 12, 1976

[54] 7-(α-CYANOMETHYLTHIO)ACETAMIDO-3-CEPHEM CARBOXYLATES

[75] Inventors: William Henry Koster, Pennington; William A. Slusarchyk, Belle Mead; Jack Bernstein, New Brunswick, all of N.J.

[73] Assignee: E. R. Squibb & Sons, Inc., Princeton, N.J.

[22] Filed: Mar. 25, 1975

[21] Appl. No.: 561,814

[52] U.S. Cl. .............................. 260/243 C; 424/246
[51] Int. Cl.² ......................................... C07D 501/16
[58] Field of Search .............................. 260/243 C

[56] References Cited
UNITED STATES PATENTS

| | | | |
|---|---|---|---|
| 3,855,212 | 12/1974 | Breuer et al. | 260/243 C |
| 3,917,587 | 11/1975 | Chauvette | 260/243 C |
| 3,917,588 | 11/1975 | Chauvette | 260/243 C |

FOREIGN PATENTS OR APPLICATIONS

| | | |
|---|---|---|
| 2,223,667 | 12/1972 | Germany |
| 2,331,133 | 1/1974 | Germany |
| 2,331,148 | 1/1974 | Germany |

OTHER PUBLICATIONS

Chauvette et al., *Chemical Abstracts*, vol. 81, 120,552a, (1974).

*Primary Examiner*—Nicholas S. Rizzo
*Assistant Examiner*—Diana G. Rivers
*Attorney, Agent, or Firm*—Lawrence S. Levinson; Merle J. Smith

[57] ABSTRACT

New 7-(α-cyanomethylthio)acetamido-3-cephem carboxylates which have the formula

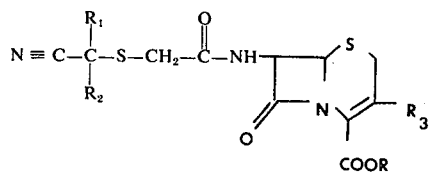

have antimicrobial activity.

14 Claims, No Drawings

7-(α-CYANOMETHYLTHIO)ACETAMIDO-3-CEPHEM CARBOXYLATES

SUMMARY OF THE INVENTION

This invention relates to new 7-(α-cyanomethylthio) acetamido-3-cephem carboxylates which have the formula

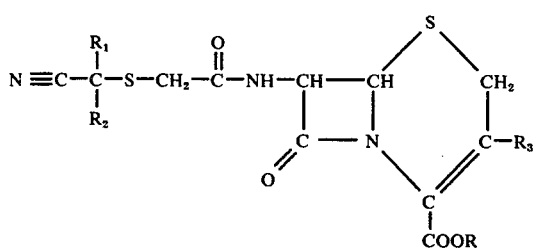

wherein R is hydrogen, alkali metal, lower alkyl, phenyl-lower alkyl or substituted phenyl-lower alkyl. $R_1$ and $R_2$ each is hydrogen or lower alkyl, and $R_3$ is hydrogen, hydroxy, halo, lower alkoxy, lower alkylsulfonyloxy, phenylsulfonyloxy or substituted phenylsulfonyloxy wherein the phenyl substituents are halo or lower alkyl.

These compounds are useful as antimicrobial agents to combat infections in susceptible animal species by microorganisms such as *Staphylococcus aureus*, *Bacillus subtilis*, *Sarcinea lutea*, *Proteus vulgaris*, *Salmonella schottmuleri* and *Klebsiella pneumonia*.

DETAILED DESCRIPTION OF THE INVENTION

The lower alkyl groups represented by the symbols in formula I are the straight and branched chain radicals of one to seven carbons in the series from methyl to heptyl. The $C_1$ to $C_4$ groups are preferred, especially methyl and ethyl.

The phenyl-lower alkyl groups are radicals having a phenyl group attached to lower alkyl groups like those described above, e.g., benzyl and phenethyl (which are preferred, especially the first) as well as such lower alkyl groups with two phenyl groups, e.g., benzhydryl. The substituted phenyl-lower alkyl groups are those having a nitro or lower alkoxy group on the phenyl ring, e.g., nitrobenzyl, methoxybenzyl (which is preferred), ethoxybenzyl and the like.

The lower alkoxy groups include lower alkyl groups like those described above linked through an oxygen, e.g., methoxy (which is preferred), ethoxy, propoxy, etc.

The halogens include the four common halogens, but chlorine and bromine are preferred, except in the case of $R_3$, chlorine, bromine and fluorine are preferred.

Preferred compounds are those wherein R is hydrogen or alkali metal, especially sodium or potassium, $R_1$ and $R_2$ each is hydrogen, and $R_3$ is hydrogen, halo, especially chloro, bromo or fluoro, lowr alkylsulfonyloxy, especially methylsulfonyloxy and substituted phenylsulfonyloxy, especially lower alkylphenylsulfonyloxy like p-toluenesulfonyloxy and halophenylsulfonyloxy like 4-fluorobenzenesulfonyloxy.

The compounds of this invention have antimicrobial activity against various pathogenic bacteria such as *Staphylococcus aureus*, *Bacillus subtilis*, *Sarcinea lutea*, *Proteus vulgaris*, *Salmonella schottmuleri*, and *Klebsiella pneumonia*. They are useful as antibacterial agents in combatting infections due to such organisms in various susceptible mammalian species such as mice, rats, domestic animals and the like. For example, a compound of formula I or a physiologically acceptable salt thereof can be used in an amount of about 1 to 50 mg/kg, preferably 4 to 20 mg/kg on a daily basis, orally or parenterally in single or two to four divided doses to treat infections of bacterial origin due to the microorganisms referred to above. These substances are administered in a conventional oral dosage form such as tablet, capsule or elixir or in an injectable form in a sterile aqueous vehicle or similar composition compounded with adjuvants, flavors, stabilizing agents, etc. as required, according to conventional pharmaceutical techniques.

The new compounds of this invention are produced from a 7-β-amino-3-cephem-4-carboxylic acid [see *J. Amer. Chem. Soc.* 96, 4986 (1974); *Helv. Chim. Acta*, 57, 1919 (1974), Netherlands Pat. No. 7,309,135]having the formula (II)

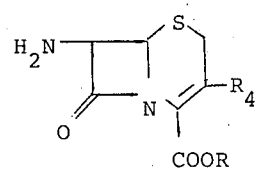

wherein $R_4$ is either hydrogen or hydroxy and R is preferably a protecting group such as nitrobenzyl, benzhydryl, benzyl, p-methoxybenzyl or the like.

The compound is acylated with a compound of the formula

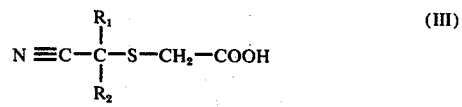

by the method described in U.S. Pat. No. 3,855,212, Dec. 17, 1974.

The product of the acylation reaction, when $R_4$ is hydroxy, which has the formula

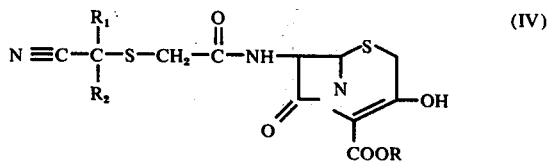

is converted to the compound of formula I wherein $R_3$ is halo, lower alkoxy, lower alkylsulfonyloxy, phenylsulfonyloxy, and substituted phenylsulfonyloxy. Treatment of the 3-hydroxy compound with a thionyl halide like thionyl chloride or thionyl bromide or with a phosphorus halide like phosphorus trichloride or phosphorus tribromide in an organic solvent inert to this reaction, e.g., dimethylformamide, dimethylacetamide, methylene chloride, benzene or mixtures of these solvents, yields a product of formula I wherein $R_3$ is the halogen corresponding to the halogen in the thionyl or phosphorus halogenating agent.

By reacting the 3-hydroxy compound of formula IV with a diazoalkane such as diazomethane, diazoethane or a triazene such as 3-ethyl-1-p-tolytriazene or 3-benzyl-1-p-tolyltriazene in an inert organic reaction medium such as methanol, ethanol, methylene chloride, chloroform, benzene, ether, ethyl acetate or the like, a compound of formula I wherein $R_3$ is lower alkoxy is obtained.

By treatment of the 3-hydroxy compound of formula IV with a lower alkylsulfonyl halide, a phenylsulfonyl halide, or a substituted phenylsulfonyl halide, in an organic solvent inert to the reaction, e.g., dimethylformamide, dimethylacetamide, dichloromethane, chloroform, benzene, dimethoxyethane, acetonitrile, and in the presence of an organic base, e.g., triethylamine, pyridine, N,N-dimethylaniline, or the like, a compound of formula I is obtained wherein $R_3$ is lower alkylsulfonyloxy, phenylsulfonyloxy or substituted phenylsulfonyloxy.

Treatment of the alkylsulfonyloxy or phenylsulfonyloxy product of formula I with potassium fluoride in the presence of a crown ether [Pedersen, JACS 89, 7017 (1967)], e.g., dicyclohexyl-18-crown-6-ether, dibenzo-18-crown-6-ether, in an inert solvent such as acetonitrile, benzene, methylene chloride yields a product of formula I wherein $R_3$ is fluorine.

Preferably, in foregoing reactions, the 4-carboxyl group is protected during the halogenation, alkylation, or acylation procedure, e.g., R in formula IV is nitrobenzyl, benzhydryl, benzyl, methoxybenzyl or the like, by methods the as those described in JACS, Helv. Chim. Acta, Netherlands Pat. No. 7,309,135, supra. The protecting group is then removed by hydrogenolysis or acid catalyzed cleavage in the presence of a carbonium ion trapping agent such as anisole yielding the product of formula I wherein R is hydrogen. Salts, such as the alkali metal salts can be formed from this product, e.g., by reaction with an alkali metal hydroxide, bicarbonate, carbonate, 2-ethylhexanoate, etc.

The intermediate of formula II wherein $R_4$ is hydrogen is prepared by the method described in Netherlands Pat. No. 7,309,135, e.g., 7-amino-3-cephem-4-carboxylic acid benzhydryl ester is derived from 7-phenylacetamido-3-cephem-4-carboxylic acid by cleavage of the amide function using phosphorus pentachloride to form an imino chloride followed by methanolysis to the corresponding imino ether with subsequent hydrolysis of the ether to the desired product. The preparation of the phenylacetyl precursor is as described in Helv. Chim. Acta 57, 1917(1974) by reduction of the 3-hydroxy cephem to a 3-hydroxy cepham. Dehydration of the 3-hydroxy cepham with acetic anhydride and triethylamine yields 7-phenylacetamido-3-cephem-4-carboxylic acid benzhydryl ester. This intermediate is then acylated as described above to obtain the product of formula I wherein $R_4$ is hydrogen.

The protecting groups are removed, for example, by hydrogenolysis, or acid catalyzed cleavage in the presence of a carbonium ion trapping agent such as anisole.

Variations for R can be obtained from the products wherein R is hydrogen by conventional means.

The starting materials of formula III are produced as described in the U.S. patent referred to above.

The following examples, which are preferred embodiments, are illustrative of the invention, providing additional process details, and serve as models for obtaining other members of the group by appropriate variation of the substitutent groups in the reactants. All temperatures are in degrees celsius.

EXAMPLE 1

7-Cyanomethylthioacetamido-3-cephem-3-ol-4-carboxylic acid Benzhydryl Ester

7-Amino-3-cephem-3-ol-4-carboxylic acid benzhydryl ester p-toluenesulfonate salt [Helv. Chim. Acta 57, 1919 (1974)], (242 mg.) is dissolved in methylene chloride (5 ml.), cooled in an ice bath, and cyanomethylthioacetyl chloride (68 mg.) in methylene chloride (3 ml.) is added, followed by 125 µl of triethylamine. The mixture is stirred for 3.5 hours at 0°–5° and then is allowed to stand overnight in the refrigerator. After diluting with methylene chloride, the reaction mixture is washed with water, then with pH 4 buffer, and dried ($Na_2SO_4$). Solvent is removed in vacuo yielding the desired product as a oil (204 mg.); NMR ($CDCl_3$, δ) 3.33 (m,$CH_2$), 3.45 (s, $NCCH_2SCH_2$—) 5.05 (d, J=4.5 Hz, $H_6$), 5.65 (q. J=4.5, 9Hz, $H_7$), 6.93 (s,$CH\phi_2$), 7.33 (s, aromatic H's), 7.80 (d, J=9Hz, NH); $\nu_{max}$ ($CH_2Cl_2$) 3380, 3310, 2225, 1785, 1735, 1690 cm$^{-1}$.

EXAMPLE 2

7-Cyanomethylthioacetamido-3-methoxy-3-cephem-4-carboxylic acid benzhydryl ester and 7-Cyanomethylthioacetamido-3-methoxy-2-cephem-4-carboxylic acid benzhydryl ester 7-Cyanomethylthioacetamido-3-cephem-3-ol-4-carboxylic acid benzhydryl ester (204 mg.) is dissolved in a minimum amount of methylene chloride and diluted with methanol (25 ml.). Then excess diazomethane in ether (generated from 0.8 g. of N-methyl-N'-nitro-N-nitrosoguanidine) is added to the solution of 7-cyanomethylthioacetamido-3-cephem-3-ol-4-carboxylic acid benzhydryl ester, cooled to 0°–5° and the mixture is allowed to stand in the cold bath for 25 minutes. Excess diazomethane is purged from solution with a stream of argon and solvent is removed in vacuo yielding a yellow oil (208 mg.). The oil is chromatographed on two preparative TLC plates (silica gel PQIF-1000, 20 × 40 cm.) developed in 1:1 ethyl acetate:chloroform. Two major bands are extracted, the band with the lower Rf being the desired 7-cyanomethylthioacetamido-3-methoxy-3-cephem-4-carboxylic acid benzhydryl ester (77 mg.); NMR ($CDCl_3$, δ) 2.95 and 3.40(ABq, J=16 Hz, $CH_2$), 3.50 (S, $NCCH_2SCH_2CO$—), 3.70 (s,$OCH_3$), 5.10 (d,J=4Hz,$H_6$), 5.57 (q, J=4,8 Hz, $H_7$), 6.95 (s,$CH\phi_2$), 7.35 (m, aromatic H's) 7.93 (d, J=8Hz, NH); $\nu_{max}$ ($CH_2Cl_2$) 2225, 1785, 1720 (sh), 690 cm$^{-1}$; and the band with the higher Rf value being the $\Delta^2$-isomer (59 mg.); NMR ($CDCl_3$, δ) 3.47 (s, $NCCH_2SCH_2CO$—), 3.57 (s, $OCH_3$), 5.03 (m, $H_4$), 5.20 (m, $H_2$), 5.28 (d, J=4 Hz, $H_6$), 5.60 (q, J=4, 9Hz, $H_7$), 6.93 (m. NH and aromatic H's); $\nu_{max}$ ($CH_2Cl_2$) 2225, 1790, 1750, 1690 cm$^{-1}$.

EXAMPLE 3

7-Cyanomethylthioacetamido-3-methoxy-3-cephem-4-carboxylic acid

7-Cyanomethylthio-3-methoxy-3-cephem-4-carboxylic acid benzhydryl ester (77 mg.) is mixed with trifluoroacetic acid (1 ml.) and anisole (50 µl) at 0°–5° and the mixture swirled in an ice bath for 10 minutes. An oily solid forms in the flask and the excess trifluoroacetic acid is removed under reduced pressure. Toluene is added to the residue and evaporated in vacuo to remove the residual trifluoroacetic acid. The residue is taken up in ethyl acetate and extracted into an aqueous solution by adjusting the pH to 8.5. After discarding the ethyl acetate layer, fresh ethyl acetate is added and the pH of the aqueous layer adjusted with 1N HCl to 1.8. Extraction of the aqueous layer is done five times with ethyl acetate and the combined extracts are dried ($Na_2SO_4$) and solvent removed in vacuo. The residue is taken up in acetone, filtered, solvent removed under a stream of argon and the residue precipitated from ethyl acetate-ether and the product 7-cyanomethylthioacetamido-3-methoxy-3-cephem-4-carboxylic acid is obtained as an amorphous powder (35 mg.); NMR ($CD_3CN$, $\delta$) 3.47 (s, $CH_2$), 3.58 (s, $NCCH_2SCH_2CO$), 3.88 (s, $OCH_3$), 5.08 (q, J=4,8 Hz, $H_7$), 7.58 (broad d, J=8Hz, NH); $\nu_{max}$ (KBr) 3310, 2240, 1760, 1655, 1590, 1530 $cm^{-1}$. Thin layer chromatography on silica gel; Rf = 0.47 (n-Bu OH—HOAc:$H_2O$ 3:1:1).

EXAMPLE 4

7-Cyanomethylthioacetamido-3-methoxy-3-cephem-4-carboxylic Acid Potassium Salt

7-Cyanomethylthioacetamido-3-methoxy-3-cephem-4-carboxylic acid (35 mg.) is dissolved in 1 ml. of methanol and 50 μl of 2.5 M potassium 2-ethyl hexanoate is added. Addition of ether causes precipitation of a very hygroscopic solid. All solvent is removed in vacuo from the mixture and the residue is solidified by the addition of acetonitrile. The desired potassium salt is collected by filtration and dried yielding 19 mg; NMR (DMSO $d_6\delta$) 3.43 (m, $CH_2$), 3.52 (s, $NCCH_2SCH_2CO$—) 3.76 (s,$OCH_3$), 4.10 (d, J=4Hz, $H_6$), 5.30 (q, J=4, 9.5 Hz, $H_7$), 9.03 (d, J=9.5 Hz,NH); $\nu_{max}$ (KBr) 3575, 3270, 2240, 1750, 1630, 1595, 1540 $cm^{-1}$.

EXAMPLE 5

3-Chloro-7-cyanomethylthioacetamido-3-cephem-4-carboxylic Acid Benzylhydryl Ester 7-Cyanomethylthioacetamido-3-cephem-3-ol-4-carboxylic acid benzhydryl ester (799 mg., 1.61 mmol.) is dissolved in anhydrous dimethylformamide (9 ml.) and phosphorus trichloride (108 μl, 1.23 mmol.) is added. The mixture is stirred at room temperature for 2 hours under an inert atmosphere then diluted with ethyl acetate and washed with 5% hydrochloric acid. The acidic aqueous layer is then extracted with ethyl acetate, the two organic layers combined, washed twice with water and dried ($Na_2SO_4$). Solvent is removed under reduced pressure and the residual oil (745 mg.) is chromatographed on six 20 × 40 cm. silica gel plates (Quantum PQIF 1000) developed in ethyl acetate. The major band with the highest Rf value contains the product 3-chloro-7-cyanomethylthioacetamido-3-cephem-4-carboxylic acid benzhydryl ester, (379 mg.): NMR ($CDCl_3,\delta$) 3.4 (m, $NCCH_2SCH_2CO$—), 3.42 and 3.77 (ABq, J=18Hz, $CH_2$), 5.00 (d, J=5Hz, $H_6$) 5.83 (q, J=5,9 Hz, $H_7$), 7.03 (s, $CH\phi_2$), 7.38 (m. aromatic H's), 7.62 (d, J=9Hz, NH); $\nu_{max}$ ($CHCl_3$) 1785, 1725, 1685 $cm^{-1}$.

EXAMPLE 6

3-Chloro-7-cyanomethylthioacetamido-3-cephem-4-carboxylic acid

3-Chloro-7-cyanomethylthioacetyl-3-cephem-4-carboxylic acid benzhydryl ester (238 mg., 0.459 mmol.) is dissolved in methylene chloride (2.5 ml.), the solution cooled to 0°–5° and anisole (60 μl, 0.55 mmol) is added followed by trifluoroacetic acid (0.75 ml.). The mixture is stirred at 0°–5° for 1.5 hour. The solvent is removed in vacuo, the residue is taken up in benzene and the solvent is again removed in vacuo to evaporate residual trifluoroacetic acid. The residue is taken up in ethyl acetate, water is added and the pH of the aqueous layer is adjusted to 7.3 while vigorously stirring. The ethyl acetate layer is separated and the aqueous layer extracted twice more with ethyl acetate. After combining the organic extracts, the solution is dried ($Na_2SO_4$) and solvent is removed under reduced pressure yielding an oil (137 mg.).

The oil is dissolved in ethyl acetate, decolorized with charcoal and filtered through Celite. The material is redissolved in ethyl acetate, dried ($Na_2SO_4$), and solvent is removed in vacuo yielding the product 3-chloro-7-cyanomethylthioacetamido-3-cephem-4-carboxylic acid as an oil (123 mg.). NMR ($CD_3CN$, $\delta$) 3.45 (s,$CH_2$), 3.57 (s, $CH_2$), 3.57 and 4.00 (ABq, J= 19Hz, $H_2$), 5.18 (d, J=5Hz, $H_6$), 5.73 (q, J=5, 8.5 Hz, $H_7$), 7.62 (d, J=8.5Hz, NH).

EXAMPLE 7

3-Chloro-7-cyanomethylthioacetamido-3-cephem-4-carboxylic Acid Potassium Salt

3-Chloro-7-cyanomethylthioacetyl-3-cephem-4-carboxylic acid (123 mg.) is dissolved in ethyl acetate and 170 μl of 2.5 M potassium 2-ethylhexanoate is added while stirring at room temperature. After a few minutes, ether is added and the precipitate is collected by filtration. The solid is washed with ethyl acetate, then with ether, and dried yielded the desired potassium salt (110 mg.): NMR ($CD_3OH$, $\delta$) 3.52 (s,$CH_2$), 3.57 (s,$CH_2$), 3.57 and 4.00 (ABq, J=18Hz, $H_2$), 5.17 (d,J=5Hz,$H_6$), 5.70 (d,J=5Hz,$H_7$); $D_{max}$ (KBr) 2240, 1755, 1665, 1605 $cm^{-1}$.

EXAMPLE 8

3-Bromo-7-cyanomethylthioacetamido-3-cephem-4-Carboxylic Acid Benzhydryl Ester

The desired product is prepared from 7-cyanomethylthioacetamido-3-cephem-3-ol-4-carboxylic acid benzhydryl ester using the procedure described in Example 5, but replacing phosphorus trichloride with phosphorus tribromide.

EXAMPLE 9

3-Bromo-7-cyanomethylthioacetamido-3-cephem-4-carboxylic acid

The benzhydryl ester of 3-bromo-7-cyanomethylthioacetamido-3-cephem-4-carboxylic acid benzhydryl ester is treated according to the procedure described in Example 6 to obtain 3-bromo-7-cyanomethylthioacetamido-3-cephem-4-carboxylic acid.

EXAMPLE 10

7-Cyanomethylthioacetamido-3-cephem-3-ol-4-Carboxylic Acid p-Nitrobenzyl Ester 7-Amino-3-hydroxy-3-cephem-4-carboxylic acid p-nitrobenzyl ester [*J. Am. Chem. Soc.* 96, 4986 (1974)] is acylated with cyanomethylthioacetyl chloride by the procedure described in Example 1 to obtain 7-cyanomethylthioacetamido-3-cephem-3-ol-4-carboxylic acid p-nitrobenzyl ester as an oil.

EXAMPLE 11

7-Cyanomethylthioacetamido-3-methoxy-3-cephem-4-Carboxylic Acid p-Nitrobenzyl Ester 7-Cyanomethylthioacetamido-3-cephem-4-carboxylic acid p-nitrobenzyl ester is alkylated with diazomethane according to the procedure sescribed in Example 2 to obtain 7described 3-methoxy-3-cephem-4-carboxylic acid p-nitrobenzyl ester as an amorphous solid.

EXAMPLE 12

7-Cyanomethylthioacetamido-3-cephem-4-Carboxylic Acid

To a solution of 1 g. of 7-cyanomethylthioacetamido-3-methoxy-3-cephem-4-carboxylic acid p-nitrobenzyl ester in 60 ml. of tetrahydrofuran and 100 ml. of methanol containing 5 drops of 1N hydrochloric acid is added 1 g. of prereduced 5% palladium on charcoal in 40 ml. of ethanol. The mixture is hydrogenated for 3 hours at room temperature at 50 psi. The catalyst is filtered and washed with tetrahydrofuran and water. The filtrate and washings are combined, solvent is removed in vacuo and the residue is taken up in an ethyl acetate water mixture. The pH of the aqueous layer is adjusted to 7.5 and the ethyl acetate is removed. Fresh ethyl acetate is added and the pH is adjusted to 2.5. The ethyl acetate layer is removed, washed with water and dried over sodium sulfate. Removal of the solvent in vacuo yields the product 7-cyanomethylthioacetamido-3-methoxy-3-cephem-4-carboxylic acid as a foam.

EXAMPLE 13

3-Chloro-7-Cyanomethylthioacetamido-3-cephem-4-Carboxylic Acid p-Nitrobenzyl Ester 7-Cyanomethylthioacetamido-3-cephem-3-ol-4-carboxylic acid p-nitrobenzyl ester is chlorinated according to the procedure described in Example 5 to obtain 3-chloro-7-cyanomethylthioacetamido-3-cephem-4-carboxylic acid p-nitrobenzyl ester as an oil.

EXAMPLE 14

3-Chloro-7-cyanomethylthioacetamido-3-cephem-4-Carboxylic Acid

The p-nitrobenzyl ester group is cleaved from 3-chloro-7-cyanomethylthioacetamido-3-cephem-4-carboxylic acid p-nitrobenzyl ester according to the procedure described in Example 12 yielding the product, 3-chloro-7-cyanomethylthioacetamido-3-cephem-4-carboxylic acid.

EXAMPLE 15

3-Bromo-7-cyanomethylthioacetamido-3-cephem-4-Carboxylic Acid p-Nitrobenzyl Ester 3-Bromo-7-cyanomethylthioacetamido-3-cephem-4-carboxylic acid p-nitrobenzyl ester is produced as an oil from 7-cyanomethylthioacetamido-3-cephem-3-ol-4-carboxylic acid p-nitrobenzyl ester using the procedure described in Example 8.

EXAMPLE 16

3-bromo-7-cyanomethylthioacetamido-3-cephem-4-Carboxylic Acid

The free acid is prepared from 3-bromo-7-cyanomethylthioacetamido-3-cephem-4-carboxylic acid p-nitrobenzyl ester of Example 15 by the procedure described in Example 12.

EXAMPLE 17

7-Cyanomethylthioacetamido-3-methylsulfonyloxy-3-cephem-4-Carboxylic Acid p-Nitrobenzyl Ester To a solution of 2.5 g. of 7-cyanomethylthioacetamido-3-cephem-3ol-4-carboxylic acid p-nitrobenzyl ester in 25 ml. of dry dimethylacetamide is added 1 ml. of propylene oxide and one equivalent of methanesulfonyl chloride. After stirring for 4 hours, the mixture is taken up in ethyl acetate and washed with saturated sodium chloride solution. Solvent is removed from the ethyl acetate solution under reduced pressure and the residue is purified by thin layer chromatography yielding the product 7-cyanomethylthioacetamido-3-methylsulfonyloxy-3-cephem-4-carboxylic acid p-nitrobenzyl ester as an amorphous solid.

EXAMPLE 18

7-Cyanomethylthioacetamido-3-methylsulfonyloxy-3-cephem-4-Carboxylic Acid

To a solution of 2 g. of cyanomethylthioacetamido-3-methylsulfonyloxy-3-cephem-4-carboxylic acid p-nitrobenzyl ester in a mixture of 15 ml. of methanol and 20 ml. of tetrahydrofuran is added 3 g. of prereduced 5% palladium on charcoal in 15 ml. of methanol. After hydrogenation for 1.5 hour, the mixture is filtered and worked up as described in Example 12 yielding the product, 7-cyanomethylthioacetamido-3-methylsulfonyloxy-3-cephem-4-carboxylic acid.

Sulfonates of 7-Cyanomethylthioacetamido-3-Cephem-3-ol-4-Carboxylic Acid

The esters and free acids shown in the table below are prepared from 7-cyanomethylthioacetamido-3-cephem-3-ol-4-carboxylic acid p-nitrobenzyl ester and the appropriate sulfonyl chloride ($RSO_2Cl$) by following the procedures described in Examples 17 and 18.

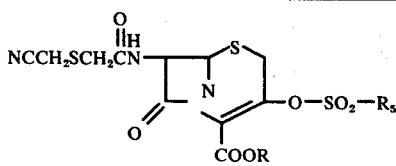

| Example | R$_s$ | R |
|---|---|---|
| 19 | —CH$_2$CH$_3$ | —CH$_2$—C$_6$H$_4$—NO$_2$ |
| 20 | —CH$_2$CH$_3$ | —H |
| 21 | —CH$_2$—CH$_2$—CH$_2$—CH$_3$ | —CH$_2$—C$_6$H$_4$—NO$_2$ |
| 22 | —CH$_2$—CH$_2$—CH$_2$—CH$_3$ | H |
| 23 | —C$_6$H$_4$—CH$_3$ | —CH$_2$—C$_6$H$_4$—NO$_2$ |
| 24 | —C$_6$H$_4$—CH$_3$ | H |
| 25 | —C$_6$H$_4$—F | —CH$_2$—C$_6$H$_4$—NO$_2$ |
| 26 | —C$_6$H$_4$—F | H |
| 27 | —C$_6$H$_5$ | —CH$_2$—C$_6$H$_4$—NO$_2$ |
| 28 | —C$_6$H$_5$ | H |

EXAMPLE 29

7-Cyanomethylthioacetamido-3-fluoro-3-cephem-4-Carboxylic Acid p-Nitrobenzyl Ester To a solution of 372 mg. of dicyclohexyl-18-crown-6-ether in 60 ml. of acetonitrile which has been dried over molecular sieves, is added 59 mg. of anhydrous potassium fluoride. The mixture is stirred for 10 minutes and then a solution of 543 mg. of 7-cyanomethylthioacetamido-3-methylsulfonyloxy-3-cephem-4-carboxylic acid p-nitrobenzyl ester in 20 ml. of acetonitrile is added. The mixture is stirred for 1 hour, then acidified with 5% hydrochloric acid and extracted with ethyl acetate. The solvent is removed from the extract under reduced pressure and the product 7-cyanomethylthioacetamido-3-fluoro-3-cephem-4-carboxylic acid p-nitrobenzyl ester is obtained after chromatography on silica gel.

EXAMPLE 30

7-Cyanomethylthioacetamido-3-fluoro-3-cephem-4-Carboxylic Acid

Cleavage of the p-nitrobenzyl ester of 7-cyanomethylthioacetamido-3-fluoro-3-cephem-4-carboxylic acid p-nitrobenzyl ester is accomplished by the method described in Example 18 yielding the product 7-cyanomethylthioacetamido-3-fluoro-3-cephem-4-carboxylic acid as an oil.

EXAMPLE 31

7-Cyanomethylthioacetamido-3-ethoxy-3-cephem-4-Carboxylic Acid Benzylhydryl Ester A solution of 3.29 g. of 7-cyanomethylthioacetamido-3-cephem-3-ol-4-carboxylic acid benzhydryl ester in 200 ml. of benzene containing 1.63 g. of 3-ethyl-1-p-tolyltriazene is refluxed for 1 hour under a nitrogen atmosphere. After removal of the solvent under reduced pressure, the residue is chromatographed on silica gel yielding the product, 7-cyanomethylthioacetamido-3-ethoxy-3-cephem-4-carboxylic acid benzhydryl ester as a foam.

EXAMPLE 32

7-Cyanomethylthioacetamido-3-ethoxy-3-cephem-4-Carboxylic Acid

Cleavage of the benzhydryl ester of 7-cyanomethylthioacetamido-3-ethoxy-3-cephem-4-carboxylic acid benzhydryl ester according to the procedure described in Example 3 yields the free acid as an amorphous powder.

EXAMPLE 33

7-Cyanomethylthioacetamido-3-cephem-4-Carboxylic Acid Benzhydryl Ester

7-Amino-3-cephem-4-carboxylic acid benzhydryl ester (366 mg.) (prepared by the method of Netherlands Patent no. 7,309,135) is dissolved in methylene chloride (5 ml.), cooled in an ice bath, and cyanomethylthioacetyl chloride (149 mg.) in methylene chloride (5 ml.) is added followed by triethylamine (101 mg.). The mixture is stirred for 4 hours at 0°–5° and, after diluting with methylene chloride the reaction mixture is washed with water then with pH 4 buffer, and dried (Na$_2$SO$_4$). The solvent is removed in vacuo yielding the product 7-cyanomethylthioacetamido-3-cephem-4-carboxylic acid benzhydryl ester as an oil.

EXAMPLE 34

7-Cyanomethylthioacetamido-3-cephem-4-Carboxylic Acid

The benzhydryl ester of 7-cyanomethylthioacetamido-3-cephem-4-carboxylic acid benzhydryl ester is cleaved according to the procedure described in Example 3 yielding the free acid as an amorphous solid.

Substituted 7-Cyanomethylthioacetamido-3-cephem-3-ol-4-Carboxylic Acid Esters The esters in the table below are prepared from (a) the appropriately substituted cyanomethylthioacetyl chloride (U.S. Pat. No. 3,855,212, Dec. 17, 1974) and (b) 7-amino-3-cephem-3-ol-4-carboxylic acid benhydryl ester or p-nitrobenzyl ester as the p-toluenesulfonte salt or free amine by the procedure of Examples 1 and 10.

| | | | |
|---|---|---|---|
| (a) $R_1R_2C(NC)$-S-CH$_2$-C(O)-Cl | (b) 7-amino cephem with COOR, OH | | product amide |

| Example | R | R$_1$ | R$_2$ |
|---|---|---|---|
| 35 | —CH(C$_6$H$_5$)$_2$ | CH$_3$ | H |
| 36 | —CH$_2$—C$_6$H$_4$—NO$_2$ | CH$_3$ | H |
| 37 | —CH(C$_6$H$_5$)$_2$ | CH$_3$ | CH$_3$ |
| 38 | —CH$_2$—C$_6$H$_4$—NO$_2$ | CH$_3$ | CH$_3$ |
| 39 | CH(C$_6$H$_5$)$_2$ | —CH$_2$CH$_3$ | H |
| 40 | —CH$_2$—C$_6$H$_4$—NO$_2$ | —CH$_2$CH$_3$ | H |
| 41 | —CH(C$_6$H$_5$)$_2$ | —CH$_2$CH$_3$ | —CH$_2$CH$_3$ |
| 42 | —CH$_2$—C$_6$H$_4$—NO$_2$ | —CH$_2$CH$_3$ | —CH$_2$CH$_3$ |

3-Substituted Cephem Esters

The 3-substituted cephem esters shown in the table below are prepared from the esters in Examples 35–42 using the method described in the example indicated.

| Example | R | R$_1$ | R$_2$ | R$_3$ | Procedure of Example |
|---|---|---|---|---|---|
| 43 | —CH(C$_6$H$_5$)$_2$ | —CH$_3$ | H | —OCH$_3$ | 2 |
| 44 | —CH(C$_6$H$_5$)$_2$ | —CH$_3$ | H | —OC$_2$H$_5$ | 31 |
| 45 | —CH(C$_6$H$_5$)$_2$ | —CH$_3$ | —CH$_3$ | —OCH$_3$ | 2 |
| 46 | —CH(C$_6$H$_5$)$_2$ | —CH$_3$ | —CH$_3$ | —OC$_2$H$_5$ | 31 |
| 47 | —CH(C$_6$H$_5$)$_2$ | CH$_2$CH$_3$ | H | —OCH$_3$ | 2 |
| 48 | —CH(C$_6$H$_5$)$_2$ | —CH$_3$ | H | Cl | 5 |
| 49 | —CH$_2$—C$_6$H$_4$—NO$_2$ | —CH$_3$ | H | Br | 15 |
| 50 | —CH$_2$—C$_6$H$_4$—NO$_2$ | —CH$_3$ | H | F | 29 |
| 51 | —CH(C$_6$H$_5$)$_2$ | —CH$_3$ | CH$_3$ | Cl | 5 |
| 52 | —CH$_2$—C$_6$H$_4$—NO$_2$ | —CH$_2$CH$_3$ | H | Cl | 13 |
| 53 | —CH$_2$—C$_6$H$_4$—NO$_2$ | —CH$_2$CH$_3$ | H | F | 29 |
| 54 | —CH$_2$—C$_6$H$_4$—NO$_2$ | —CH$_3$ | H | —SO$_2$CH$_3$ | 17 |

-continued

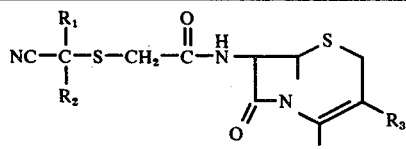

| Example | R | $R_1$ | $R_2$ | $R_3$ | Procedure of Example |
|---|---|---|---|---|---|
| 55 | —CH₂—C₆H₄—NO₂ | —CH₃ | H | —SO₂—C₆H₁₀—CH₃ | 23 |
| 56 | —CH₂—C₆H₄—NO₂ | —CH₃ | H | —SO₂—C₆H₁₀—F | 25 |
| 57 | —CH₂—C₆H₄—NO₂ | —CH₂—CH₃ | H | —SO₂CH₂CH₃ | 19 |
| 58 | —CH₂—C₆H₄—NO₂ | —CH₃ | —CH₃ | —SO₂CH₃ | 17 |
| 59 | —CH₂—C₆H₄—NO₂ | —CH₂CH₃ | H | —SO₂CH₃ | 17 |

3-Cephem Esters

The 3-cephem esters (c) in the table below are prepared from (a) the appropriately substituted cyanomethylacetyl chloride (U.S. Pat. No. 3,855,212, Dec. 17, 1974) and (b) 7-amino-3-cephem-4-carboxylic acid benzhydryl ester using the method described in Example 33.

3-Cephem Carboxylates

The 3-cephem carboxylates in the table below are prepared from the esters in Examples 43–59 by removal of the p-nitrobenzyl or benzhydryl ester groups by the methods described in Examples 12 or 3, respectively. The salts in the table are prepared from the carboxylic acids by the method of Example 7.

| Example | $R_1$ | $R_2$ |
|---|---|---|
| 60 | —CH₃ | H |
| 61 | —CH₃ | —CH₃ |
| 62 | —CH₂CH₃ | H |
| 63 | —CH₂CH₃ | —CH₂CH₃ |

| Example | R | $R_1$ | $R_2$ | $R_3$ |
|---|---|---|---|---|
| 64 | H | —CH₃ | H | —OCH₃ |
| 65 | K | —CH₃ | H | —OC₂H₅ |
| 66 | Na | —CH₃ | —CH₃ | —OCH₃ |
| 67 | H | —CH₃ | —CH₃ | —OC₂H₅ |
| 68 | H | —CH₂CH₃ | H | —OCH₃ |
| 69 | K | —CH₃ | H | Cl |
| 70 | K | —CH₃ | H | Br |
| 71 | H | —CH₃ | H | F |
| 72 | —CH₂C₆H₅ | —CH₃ | —CH₃ | Cl |
| 73 | H | —CH₂CH₃ | H | Cl |
| 74 | Na | —CH₂CH₃ | H | F |
| 75 | H | —CH₃ | H | —SO₂CH₃ |

-continued

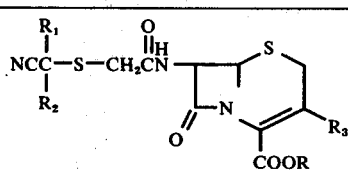

| Example | R | $R_1$ | $R_2$ | $R_3$ |
|---|---|---|---|---|
| 76 | —$CH_3$ | —$CH_2CH_2CH_3$ | H | —$SO_2$—⌬—$CH_3$ |
| 77 | H | —$CH_3$ | H | —$SO_2$—⌬—F |
| 78 | H | —$CH_2CH_3$ | H | —$SO_2$—$CH_2CH_3$ |
| 79 | H | —$CH_3$ | —$CH_3$ | —$SO_2CH_3$ |
| 80 | $C_2H_5$ | —$CH_2CH_3$ | H | —$SO_2CH_3$ |
| 81 | H | —$CH_3$ | H | H |
| 82 | K | —$CH_3$ | —$CH_3$ | H |
| 83 | —$CH_3$ | —$CH_2CH_3$ | H | H |
| 84 | Na | —$CH_2CH_3$ | —$CH_2CH_3$ | H |

What is claimed is:

1. A compound of the formula

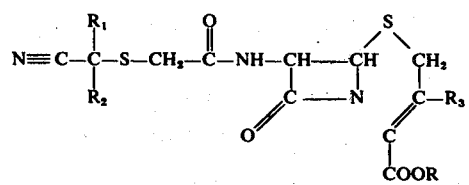

wherein R is hydrogen, alkali metal, lower alkyl, phenyl-lower alkyl, substituted phenyl-lower alkyl wherein the phenyl substituents are nitro or lower alkyoxy, or benzhydryl; $R_1$ and $R_2$ each is hydrogen or lower alkyl; and $R_3$ is hydroxy, chloro, bromo, fluoro or lower alkoxy said lower alkyl and lower alkoxy groups having one to seven carbons.

2. A compound as in claim 1 wherein R is hydrogen or alkali metal; $R_1$ and $R_2$ each is hydrogen; and $R_3$ is chloro, bromo or fluoro.

3. A compound as in claim 1 wherein R, $R_1$ and $R_2$ each is hydrogen.

4. A compound as in claim 1 wherein $R_3$ is chloro, bromo or fluoro.

5. A compound as in claim 1 wherein $R_3$ is hydroxy.

6. A compound as in claim 1 wherein $R_3$ is lower alkoxy.

7. A compound as in claim 1 wherein $R_3$ is hydroxy; R is benzhydryl; and $R_1$ and $R_2$ each is hydrogen.

8. A compound as in claim 3 wherein $R_3$ is lower alkoxy.

9. A compound as in claim 8 wherein the lower alkoxy group is methoxy.

10. A compound as in claim 3 wherein $R_3$ is chloro.

11. A compound as in claim 3 wherein $R_3$ is fluoro.

12. A compound as in claim 3 wherein $R_3$ is bromo.

13. A compound as in claim 1 wherein R is benzhydryl.

14. A compound as in claim 1 wherein R is p-nitrobenzyl.

* * * * *